United States Patent
Silvestrini et al.

[11] Patent Number: 6,001,865
[45] Date of Patent: Dec. 14, 1999

[54] 3-SUBSTITUTED 1-BENZYL-1H-INDAZOLE DERIVATIVES AS ANTIFERTILITY AGENTS

[75] Inventors: Bruno Silvestrini, Rome, Italy; C. Yan Cheng, Staten Island, N.Y.

[73] Assignee: Angelini Pharmaceuticals Inc., River Edge, N.J.

[21] Appl. No.: 09/304,042

[22] Filed: May 4, 1999

[51] Int. Cl.⁶ ........................ A61K 31/415; C07D 231/56
[52] U.S. Cl. ........................................ 514/403; 548/362.5
[58] Field of Search ........................ 548/362.5; 514/403

[56] References Cited

U.S. PATENT DOCUMENTS

| | | |
|---|---|---|
| 3,895,026 | 7/1975 | Palazzo et al. |
| 3,956,312 | 5/1976 | Magdinyl et al. ................ 548/362.5 |

OTHER PUBLICATIONS

Giorgio Corsi, et al. "1–Halobenzyl–1H–indazole–3–carboxylic Acids. A New Class of Antispermatogenic Agents", The Journal of Medicinal Chemistry, vol. 19, No. 6, 1976, pp. 778–783.

*Primary Examiner*—Robert W. Ramsuer
*Attorney, Agent, or Firm*—Oblon, Spivak, McClelland, Maier & Neustadt, P.C.

[57] ABSTRACT

An indazole derivative of formula (I)

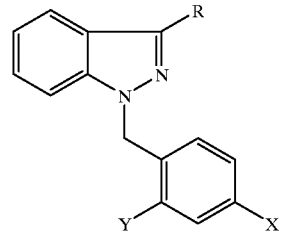

wherein

R is selected from the group comprising —$CONHNH_2$, —$CONHN(CH_3)_2$ and —CH=CH—COOH, X and Y, the same or different from each other, are halogen, and salts thereof and an antifertility composition comprising the same.

5 Claims, No Drawings

3-SUBSTITUTED 1-BENZYL-1H-INDAZOLE DERIVATIVES AS ANTIFERTILITY AGENTS

The present invention relates to 3-substituted 1-benzyl-1H-indazole derivatives endowed with antifertility activity and a composition containing the same.

U.S. Pat. No. 3,895,026 describes some 3-substituted derivatives of 1-benzyl-1H-indazole such as, for examples, 3-carboxylic acid, 3-carboxamide, β-glyceryl-3 carboxylate, β-ethylene glycole-3 carboxylate. A structure-activity study showed that some of these 3-substituted derivatives of 1-benzyl-1H-indazole compounds are endowed with anti-spermatogenic properties ("J. Med. Chem.", 19, 778, 1976).

Now, it has been surprisingly found a family of indazole derivatives which shows an antifertility activity useful in contrasting the spread of infestant animals such as rats, pigeons and mice.

It is therefore a first object of the present invention to provide an indazole derivative of formula (I)

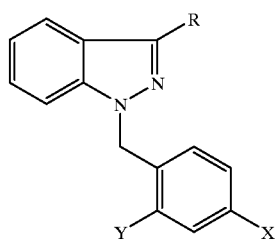

(I)

wherein

R is selected from the group comprising —CONHNH$_2$, —CONHN(CH$_3$)$_2$ and —CH=CH—COOH, X and Y, the same or different from each other, are halogen, and salts thereof.

Preferably, both X and Y are Cl.

The compounds of this invention may be readily prepared according to conventional techniques.

It is also another object of the present invention to provide a composition comprising an effective amount of a compound of formula (I) or a salt thereof together with at least an inert excipient.

Preferably, the composition of this invention is prepared in a suitable dosage form comprising an effective dose of at least a compound of formula (I) or a salt thereof and at least an inert excipient.

Examples of suitable dosage forms are powders, granules, and solutions.

The dosage forms may also contain other conventional ingredients as preservatives, stabilizers, sweeteners, colouring agents, flavouring agents and the like.

When required by particular conditions, the composition of the present invention may contain also other active ingredients whose concomitant administration is useful.

The amount of the compound of formula (I) or of a salt thereof in the composition of the present invention may vary in a rather wide range depending on known factors such as, for instance, the body weight of the infestant animal, the dosage form, and the activity of the chosen compound of formula (I). The optimum dose can nevertheless easily be established by a person skilled in the art by routine procedures.

Typically, the amount of the compound of formula (I) or of a salt thereof in the composition of the present invention will be such that it insures an administration level of from 50 to 400 mg/Kg/day p.o.

The dosage forms of the composition of the present invention can be prepared according to techniques which are known in the art and comprise procedures such as mixing, granulation, compression, solubilization, and the like.

The present invention is further described by the following Examples and Assays which are for illustrative purpose only and should not be construed as a limitation of the invention.

EXAMPLE 1

1-(2,4-dichlorobenzyl)-indazole-3-acrilic Acid (AF-2785) (I: X=Y=—Cl, R=—CH=CHCOOH)

A mixture of melted CH$_3$COOK (3 g, 0.03 moles), 1-(2,4-dichlorobenzyl)-indazole-3-carboxaldehyde (14.2 g, 0.047 moles) and (CH$_3$CO)$_2$O (7.5 ml, 0.08 moles) was heated at 160° C. for 6 hours. The reaction mixture was then cooled at 50° C. and partitioned between H$_2$O and ethyl acetate. The residue of the organic phase was recrystallized firstly from acetic acid and then twice from isopropyl alcohol to give the title compound (8.5 g), m.p. 198–199° C.

| Elemental analysis for C$_{17}$H$_{12}$Cl$_2$N$_2$O$_2$ | C | H | N |
|---|---|---|---|
| % found | 58.65 | 3.38 | 8.10 |
| % calculated | 58.81 | 3.48 | 8.07 |

$^1$H NMR (DMSO, δ); 5.80 (s, 2H, CH$_2$-Ar); 6.74 (d, 1H, J=16 Hz, CH=CH—COOH); 7.82 (d,1 H, J=16 Hz, CH=CH—COOH); 7.2–8.2 (m, 7H, Ar).

EXAMPLE 2

1-(2,4-dichlorobenzyl)-indazole-3-carbohydrazide (AF-2364) (I: X=Y=—Cl, R=—CONHNH$_2$)

To a solution of 1-(2,4-dichlorobenzyl)-indazole-3-carboxylic acid methyl ester (12.5 g) in acetic acid (25 ml), at the temperature of 100° C. and under stirring, a solution of 85% hydrazine hydrate (100 ml) was slowly added. After 1 hour at reflux temperature the reaction mixture was cooled and filtered. The obtained solid was washed with H$_2$O (2×150 ml) and recrystallized from ethyl alcohol to give the title compound (11.5 g), m.p.161–162° C.

| Elemental analysis for C$_{15}$H$_{12}$Cl$_2$N$_4$O | C | H | N |
|---|---|---|---|
| % found | 53.70 | 3.55 | 16.80 |
| % calculated | 53.75 | 3.61 | 16.72 |

$^1$H NMR (DMSO, δ); 4.50 (s, 2H, NH$_2$); 1.96 (s, 2H, CH$_2$-Ar); 6.8–8.3 (m, 7H, Ar); 9.6 (s, 1 H, NH).

General Procedure

Two sets of Sprague-Dawley adult rats (body weight= about 250 g, on day 0), designated group 1 (n=5 or 6) and group 2 (n=4), were used in animal studies. Drugs were suspended in 0.25% (w/v) methyl cellulose at a concentration of 20 mg/ml.

Assay 1

Antifertility Activity of AF-2364

In Group 1, rats (n=5) received a dose of AF-2364 at 50 mg/kg body weight by gavage on day 0. These rats received another oral dose of AF-2364 at 50 mg/kg body weight every 2-days (i.e. on day 2, 4, and 6) until a total of 4 doses were administered. Control rats (n=6) received vehicle only. For mating experiments, each treated male rat was mated separately with a virgin female in an isolated cage on day 20, 42, 63, 84, 112 and 136 after the administration of the first dose of AF-2364. Mating was confirmed by the presence of cervical plugs. Once mating had occurred, the female was removed and housed individually for 21–25 days to allow gestation to proceed to completion. Pups, if any, were counted and examined for gross abnormalities.

The results are shown in the following Table 1.

TABLE 1

| Compound | Days | Fertility Efficacy (%) | Litter size (average) |
| --- | --- | --- | --- |
| AF-2364 | 20 | 100 | 15.2 ± 1.3 |
|  | 42 | 20 | 6 |
|  | 63 | 20 | 11 |
|  | 84 | 40 | 13.5 ± 0.5 |
|  | 112 | 40 | 14.5 ± 0.5 |
|  | 136 | 40 | 15 ± 0 |
| Control | 136 | 100 | 14.8 ± 2.3 |

Table 1 shows that for Control rats, the fertility rate was 100% with an average litter size of 14.8±2.3 (n=6), while AF-2364 had no effect on day 20, the fertility was reduced to about 20% on days 42 and 63 where only one rat (out of 5) could give birth to a litter size of 6 and 11, respectively. On days 84, 112 and 136, an additional rat regained its fertility. In the treated animals with rebouncing fertility, the litter size and the pups appeared to be normal without any gross abnormalities.

The above result also demonstrates the reversibility of the treatment. These animals are currently being mated on a biweekly basis to assess whether full fertility can be regained.

Assay 2

Antifertility activity of AF-2364

In Group 2, rats (n=4) received a dose of AF-2364 at 50 mg/kg body weight by gavage on day 0. These rats received another oral dose of AF-2364 at 50 mg/kg body weight every 2-week until a total of 6 doses were administered. Control rats (n=6) received vehicle only. For mating experiments, each treated rat was mated separately with a virgin female in an isolated cage on day 42, 56, 70, 84, 98, 112, and 126 after the administration of the first dose of AF-2364 using procedures as described in the General procedure above.

The results are shown in the following Table 2.

TABLE 2

| Compound | Days | Fertility Efficacy (%) | Litter size (average) |
| --- | --- | --- | --- |
| AF-2364 | 42 | 50 | 12.5 ± 3.5 |
|  | 56 | 0 | 0 |
|  | 70 | 0 | 0 |
|  | 84 | 0 | 0 |
|  | 96 | 0 | 0 |
|  | 112 | 0 | 0 |
|  | 126 | 0 | 0 |
| Control | 126 | 100 | 14.8 ± 2.3 |

Table 2 shows that, while the effect of AF-2364 on rats by day 42 was similar to that described in the previous Assay 1, this treatment regimen appears to be more effective since the fertility in all rats in this group was reduced to 0% up to 126 day. These rats will continue to be mated every 2 weeks to access the reversibility of fertility after cessation of the drug use.

Assay 3

Antifertility Activity of AF-2785

In Group 1, rats (n=6) received a dose of AF-2785 at 50 mg/kg body weight by gavage on day 0. These rats received another oral dose of AF-2785 at 50 mg/kg b.w. every 2-days until a total of 5 doses were administered. An additional dose was used for these animals versus AF-2364 (see the previous Assay 1) since preliminary histological analysis revealed that this compound is less potent than AF-2364 in view of its antifertility effects.

The following Table 3.

TABLE 3

| Compound | Days | Fertility Efficacy (%) | Litter size (average) |
| --- | --- | --- | --- |
| AF-2785 | 14 | 100 | 13.7 ± 2.1 |
|  | 20 | 66.67 | 15.5 ± 3.3 |
|  | 42 | 16.67 | 14 |
|  | 63 | 83.33 | 13.6 ± 1.7 |
|  | 84 | 100 | 16 ± 2.7 |
|  | 112 | 100 | 14.4 ± 0.9 |
| Control | 112 | 100 | 14.8 ± 2.3 |

Table 3 shows that its anti-fertility efficacy reached a level of 16.67% (only one out of the 6 treated rats can cause pregnancy in the virgin female) by day 42. Rats regained their fertility very rapidly illustrating this is also a potential male contraceptive.

Assay 4

Antifertility Activity of AF-2785

In Group 2, rats (n=4) received a dose of AF-2785 at 50 mg/kg body weight by gavage on day 0. These rats received another oral dose of AF-2785 every 2-weeks until a total of 8 doses were administered.

The results are shown in the following Table 4.

TABLE 4

| Compound | Days | Fertility Efficacy (%) | Litter size (average) |
| --- | --- | --- | --- |
| AF-2785 | 42 | 100 | 13.5 ± 4.66 |
|  | 56 | 75 | 12.7 ± 4.2 |
|  | 70 | 75 | 12.3 ± 2.5 |
|  | 84 | 75 | 13.7 ± 3.2 |
|  | 98 | 75 | 16 ± 1 |
|  | 112 | 100 | 11.3 ± 5.7 |
| Control | 112 | 100 | 14.8 ± 2.3 |

Table 4 shows that when the drug was administered 2-weeks apart, it was less effective than when it was fed more frequently (Table 3 versus Table 4).

We claim:

1. An indazole derivative of formula (I)

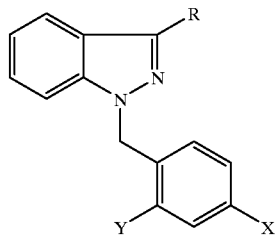

(I)

wherein

R is selected from the group comprising —$CONHNH_2$, —$CONHN(CH_3)_2$ and —CH=CH—COOH, X and Y, the same or different from each other, are halogen, and salts thereof.

2. An indazole derivative according to claim 1, characterized in that both X and Y are Cl.

3. An indazole derivative according to claim 1, characterized in that R=—$CONHNH_2$ and X=Y=Cl.

4. An indazole derivative according to claim 1, characterized in that R=—CH=CH—COOH and X=Y=Cl.

5. An antifertility composition comprising an effective amount of a compound of formula (I) or a salt thereof together with at least an inert excipient.

* * * * *